United States Patent [19]

Berg et al.

[11] Patent Number: 4,507,176
[45] Date of Patent: Mar. 26, 1985

[54] SEPARATION OF N-BUTYL ACETATE FROM N-BUTANOL BY EXTRACTIVE DISTILLATION

[76] Inventors: Lloyd Berg, 1314 S. Third Ave.; An-I Yeh, 709 S. 12th Ave., both of Bozeman, Mont. 59715

[21] Appl. No.: 608,071

[22] Filed: May 7, 1984

[51] Int. Cl.³ ............................ B01D 3/40; C07C 67/48
[52] U.S. Cl. ........................................ 203/51; 203/18; 203/56; 203/57; 203/60; 203/59; 203/64; 203/58; 560/248
[58] Field of Search ............... 203/51, 52, 18, 50, 203/59, 57, 60, 64, 56, 14, 19, 63, 58, 68; 568/594; 560/248

[56] References Cited

U.S. PATENT DOCUMENTS

| | | | |
|---|---|---|---|
| 1,836,096 | 12/1931 | Van Schaack, Jr. | 560/248 |
| 1,854,385 | 4/1932 | Van Schaack | 568/594 |
| 3,689,372 | 9/1972 | Sugano et al. | 203/57 |
| 4,379,028 | 4/1983 | Berg et al. | 203/60 |
| 4,431,838 | 2/1984 | Feldman et al. | 560/248 |
| 4,473,444 | 9/1984 | Feldman et al. | 560/248 |

FOREIGN PATENT DOCUMENTS

| | | | |
|---|---|---|---|
| 160217 | 12/1975 | Japan | 203/57 |
| 4119411 | 9/1978 | Japan | 203/64 |
| 0765334 | 1/1957 | United Kingdom | 203/60 |

Primary Examiner—Wilbur Bascomb
Assistant Examiner—Virginia Manoharan

[57] ABSTRACT n-Butyl acetate cannot be completely removed from n-butyl acetate-n-butanol—water mixtures by distillation because of the presence of the minimum ternary azeotrope. n-Butyl acetate can be readily removed from mixtures containing it, n-butanol and water by using extractive distillation in which the extractive distillation agent is a higher boiling oxygenated, nitrogenous and-/or sulfur containing organic compound or a mixture of these. Typical examples of effective agents are N,N-dimethylacetamide, dimethylsulfoxide and acetamide, ethylene glycol propylene glycol, dimethylsulfoxide and acetamide.

2 Claims, No Drawings

SEPARATION OF N-BUTYL ACETATE FROM N-BUTANOL BY EXTRACTIVE DISTILLATION

FIELD OF THE INVENTION

This invention relates to a method for separating n-butyl acetate from n-butanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the commercially important ways to manufacture n-butyl acetate is by the catalytic esterification of n-butanol with acetic acid. n-Butyl acetate (b.p.=126.1° C.), n-butanol (b.p.=117.7° C.) and water (b.p.=100° C.) form a ternary azeotrope boiling at 90.7° C. and containing 63 weight percent n-butyl acetate, 8 wt.% n-butanol and 29 wt.% water. n-Butyl acetate also forms a binary azeotrope with n-butanol which boils at 117.6° C. and contains 32.8 wt.% n-butyl acetate, and a binary azeotrope with water boiling at 90.7° C. containing 72.9 wt.% n-butyl acetate. n-Butanol also forms a binary minimum azeotrope with water which boils at 93° C. and contains 55.5 wt.% n-butanol. Thus in the esterification of n-butanol with acetic acid to form n-butyl acetate and water, the rectification of this mixture has three binary and a ternary azeotrope to contend with, and yields the lowest boiling constituent, namely the n-butyl acetate-n-butanol-water ternary azeotrope. It is therefore impossible to produce n-butyl acetate from n-butanol and water mixtures by rectification because the lower boiling ternary azeotrope will always come off overhead as the initial product. Any mixture of n-butyl acetate, n-butanol and water subjected to rectification at one atmosphere pressure will produce an overhead product boiling at 90.7° C. and containing 63 wt.% n-butyl acetate, 8 wt.% n-butanol and 29 wt.% water. Extractive distillation would be an attractive method of effecting the separation of n-butyl acetate from n-butanol if agents can be found that (1) will break the n-butyl acetate-n-butanol-water azeotrope and (2) are easy to recover from the n-butanol, that is, form no azeotrope with n-butanol and boil sufficiently above n-butanol to make the separation by rectification possible with only a few theoretical plates.

Extractive distillation typically requires the addition of an equal amount to twice as much extractive agent as the n-butyl acetate-n-butanol-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with n-butanol otherwise it will form a two phase azeotrope with the n-butanol in the recovery column and some other method of separation will have to be employed.

The breaking of this azeotrope by extractive distillation is a new concept. The closest application of the concept might be the breaking of the methyl acetate-methanol azeotrope reported by Yoshida & Oka in Japanese patent 54/119-411, Sept. 17, 1979 and by Berg & Yeh, CHEMICAL ENGINEERING COMMUNICATIONS, p.3219–3223, 1984.

OBJECTIVE OF THE INVENTION

The object of this invention is to provide a process or method of extractive distillation that will enhance the relative volatility of n-butyl acetate from n-butanol in their separation in a rectification column. It is a further object of this invention to identify suitable extractive distillation agents which will eliminate the n-butyl acetate-n-butanol-water ternary azeotrope and make possible the production of pure n-butyl acetate and n-butanol by rectification. It is a further object of this invention to identify organic compounds which, in addition to the above constraints, are stable, can be separated from n-butanol by rectification with relatively few theoretical plates and can be recycled to the extractive distillation column and reused with little decomposition.

SUMMARY OF THE INVENTION

The objects of the invention are provided by a process for separating n-butyl acetate from n-butanol which entails the use of certain oxygenated, nitrogenous and/or sulfur containing organic compounds as the agent in extractive distillation.

DETAILED DESCRIPTION OF THE INVENTION

We have discovered that certain oxygenated, nitrogenous and/or sulfur containing organic compounds, some individually but principally as mixtures, will effectively negate the n-butyl acetate-n-butanol-water ternary azeotrope and permit the separation of pure n-butyl acetate from n-butanol by rectification when employed as the agent in extractive distillation. Tables 1, 2, 3 and 4 list the compounds, mixtures and approximate proportions that we have found to be effective. The data in Tables 1-4 were obtained in a vapor-liquid equilibruim still. In each case, the starting material was the n-butyl acetate-n-butanol-water azeotrope. The ratios are the parts by weight of extractive agent used per part of n-butyl acetate-n-butanol-water azeotrope. The relative volatilities are listed for each of the two ratios employed. The compounds that are effective as extractive distillation agents when used alone are ethylene glycol and N,N-dimethylacetamide. The compounds which are effective when used in mixtures of two or more components are acetamide, dimethylsulfoxide, dimethylformamide, ethylene glycol, propylene glycol, 1,3-propanediol, 1,4-butanediol, 1,5-pentanediol, 1,6-hexanediol, diethylene glycol, triethylene glycol, tetraethylene glycol, dipropylene glycol, polypropylene glycol, formamide, ethylene carbonate, propylene carbonate, triethanolamine, glycerine, N,N-dimethylacetamide, 1,3-butanediol, neopentyl glycol, hexylene glycol, 1,2,6-hexanetriol, polyethylene glycol, quinoline, nitrobenzene, adiponitrile, sulfolane, dibutyl phthalate, isophorone, The two relative volatilities shown in Tables 1-4 correspond to the two different ratios employed. For example in Table 2, one part of N,N-dimethylacetamide with one part of n-butyl acetate-n-butanol-water azeotrope gives a relative volatility of 2.03, 6/5 parts of N,N-dimethylacetamide gives 1.38. One half part of DMSO mixed with one half part of N,N-dimethylacetamide with one part of n-butyl acetate-n-butanol-water azeotrope gives a relative volatility of 1.76, 3/5 parts of DMSO plus 3/5 parts of N,N-dimethylacetamide gives 2.17. One third parts of DMSO plus ⅓ parts of N,N-dimethylacetamide plus ⅓ parts of propylene glycol mixed with one parts of n-butyl acetate-n-butanol-water azeotrope gives a relative volatility of 1.61, with 2/5 parts, these three give 1.78. In every example in Tables 1-4, the starting material is the n-butyl acetate-n-butanol-water azeotrope which possesses a relative volatility of 1.00.

Several of the compounds and mixtures listed in Tables 1-4 and whose relative volatility has been determined in the vapor-liquid equilibrium still, were then evaluated in a glass perforated plate rectification column possessing 4.5 theoretical plates. The n-butyl acetate-n-butanol-water mixture studied contained 86 wt.% n-butyl acetate, 11 wt.% n-butanol, 3 wt.% water. The n-butyl acetate-n-butanol-water azeotrope contains 63 wt.% n-butyl acetate, 8 wt.% n-butanol and 29 wt.% water. In every case, the overhead is richer than 63 wt.% n-butyl acetate and the results are tabulated in Table 5. Without the extractive agent, the overhead would be the azeotrope, 63 wt.% n-butyl acetate. This proves that the extractive agent is negating the azeotrope and makes the rectification proceed as if the azeotrope no longer existed and brings the more volatile components, n-butyl acetate and water, out as the overhead products. It is our belief that this is the first time that this has been accomplished for this azeotrope.

The data in Table 5 was obtained in the following manner. The charge was 86 wt.% n-butyl acetate, 11 wt.% n-butanol and 3 wt.% water and after a half hour of operation in the 4.5 theoretical plate column to establish equilibrium, ethylene glycol at 50° C. and 20 ml/min. was pumped in. The rectification was continued for two hours with sampling of overhead and bottoms after one hour, 1.5 hours and two hours. The average of the three analyses is shown in Table 5 and was 96.78 wt.%

TABLE 1

Extractive Distillation Agents That Are Effective In Separating
n-Butyl acetate From n-Butanol Which Contain Acetamide

| Compounds | Ratios | | Relative Volatilities | |
|---|---|---|---|---|
| Acetamide, Dimethylsulfoxide (DMSO) | (½)[2] | (3/5)[2] | 1.55 | 1.92 |
| Acetamide, Dimethylformamide | " | " | 1.60 | 1.52 |
| Acetamide, Ethylene glycol | " | " | 1.90 | 1.79 |
| Acetamide, 1,3-Propanediol | " | " | 1.64 | 1.73 |
| Acetamide, Propylene glycol | " | " | 1.69 | 1.54 |
| Acetamide, 1,4-Butanediol | " | " | 1.78 | 1.60 |
| Acetamide, 1,5-Pentanediol | " | " | 1.55 | 1.60 |
| Acetamide, 1,6-Hexanediol | " | " | 1.74 | 1.44 |
| Acetamide, Diethylene glycol | " | " | 1.77 | 1.73 |
| Acetamide, Triethylene glycol | " | " | 2.14 | 1.79 |
| Acetamide, Dipropylene glycol | " | " | 1.28 | 1.22 |
| Acetamide, Polypropylene glycol | " | " | 1.20 | 1.28 |
| Acetamide, Formamide | " | " | 1.37 | 1.63 |
| Acetamide, Ethylene carbonate | " | — | 1.43 | — |
| Acetamide, Propylene carbonate | " | " | 1.07 | 1.27 |
| Acetamide, Triethanolamine | " | " | 1.14 | 1.92 |
| Acetamide, DMSO, Ethylene glycol | (⅓)[3] | (2/5)[3] | 1.99 | 1.80 |
| Acetamide, DMSO, propylene glycol | " | " | 1.58 | 1.76 |
| Acetamide, DMSO, 1,4-Butanediol | " | " | 1.87 | 1.80 |
| Acetamide, DMSO, 1,5-Pentanediol | " | " | 1.29 | 1.82 |
| Acetamide, DMSO, 1,6-Hexanediol | " | " | 1.47 | 1.77 |
| Acetamide, DMSO, Diethylene glycol | " | " | 1.84 | 1.87 |
| Acetamide, DMSO, Triethylene glycol | " | " | 1.66 | 2.21 |
| Acetamide, DMSO, Dipropylene glycol | " | " | 1.49 | 1.42 |
| Acetamide, DMSO, polypropylene glycol | " | " | 1.63 | 1.33 |
| Acetamide, DMSO, Triethanolamine | " | " | 1.71 | 2.21 |
| Acetamide, DMSO, Ethylene carbonate | " | — | 1.47 | — |
| Acetamide, Dimethylformamide, Glycerin | " | " | 1.68 | 1.43 |
| Acetamide, Dimethylformamide, Triethanolamine | " | " | 1.48 | 1.64 |
| Acetamide, N,N—Dimethylacetamide, Triethanolamine | " | " | 1.69 | 1.65 |

TABLE 1-continued

Extractive Distillation Agents That Are Effective In Separating
n-Butyl acetate From n-Butanol Which Contain Acetamide

| Compounds | Ratios | | Relative Volatilities | |
|---|---|---|---|---|
| Acetamide, N,N—Dimethylacetamide, 1,3-Propanediol | " | " | 1.84 | 1.85 |

TABLE 2

Extractive Distillation Agents That Are Effective in Separating
n-Butyl acetate From n-Butanol Which Contain N,N—Dimethylacetamide

| Compounds | Ratios | | Relative Volatilities | |
|---|---|---|---|---|
| N,N—Dimethylacetamide | 1 | 6/5 | 2.03 | 1.38 |
| N,N—Dimethylacetamide, Dimethylsulfoxide (DMSO) | $(\frac{1}{2})^2$ | $(3/5)^2$ | 1.76 | 2.17 |
| N,N—Dimethylacetamide, Formamide | " | " | 1.31 | 1.37 |
| N,N—Dimethylacetamide, Dimethylformamide | " | " | 1.50 | 1.43 |
| N,N—Dimethylacetamide, Acetamide | " | " | 1.61 | 1.27 |
| N,N—Dimethylacetamide, Ethylene glycol | " | " | 1.58 | 1.65 |
| N,N—Dimethylacetamide, 1,3-Propanediol | " | " | 1.31 | 1.49 |
| N,N—Dimethylacetamide, Propylene glycol | " | " | 1.16 | 1.27 |
| N,N—Dimethylacetamide, 1,3-Butanediol | " | " | 1.48 | 1.30 |
| N,N—Dimethylacetamide, 1,4-Butanediol | " | " | 1.46 | 1.35 |
| N,N—Dimethylacetamide, 1,5-Pentanediol | " | " | 1.25 | 1.29 |
| N,N—Dimethylacetamide, Neopentyl glycol | " | " | 1.07 | 1.25 |
| N,N—Dimethylacetamide, 1,6-Hexanediol | " | " | 1.32 | 1.34 |
| N,N—Dimethylacetamide, Hexylene glycol | " | " | 1.14 | 1.05 |
| N,N—Dimethylacetamide, Diethylene glycol | " | " | 1.52 | 1.36 |
| N,N—Dimethylacetamide, Triethylene glycol | " | " | 1.22 | 1.37 |
| N,N—Dimethylacetamide, Tetraethylene glycol | " | " | 1.16 | 1.37 |
| N,N—Dimethylacetamide, Dipropylene glycol | " | " | 1.40 | 1.13 |
| N,N—Dimethylacetamide, Glycerine | " | " | 1.49 | 1.69 |
| N,N—Dimethylacetamide, 1,2,6-Hexanetriol | " | " | 1.75 | 1.98 |
| N,N—Dimethylacetamide, Polyethylene glycol | " | " | 1.45 | 1.39 |
| N,N—Dimethylacetamide, Triethanolamine | " | " | 1.37 | 1.55 |
| N,N—Dimethylacetamide, DMSO, Acetamide | $(\frac{1}{3})^3$ | $(2/5)^3$ | 1.92 | 1.80 |
| N,N—Dimethylacetamide, DMSO, Ethylene glycol | " | " | 1.66 | 1.50 |
| N,N—Dimethylacetamide, DMSO, Propylene glycol | " | " | 1.61 | 1.78 |
| N,N—Dimethylacetamide, DMSO, 1,3-Butanediol | " | " | 1.21 | 1.49 |
| N,N—Dimethylacetamide, DMSO, 1,4-Butanediol | " | " | 1.52 | 1.85 |
| N,N—Dimethylacetamide, DMSO, 1,5-Pentanediol | " | " | 1.90 | 2.25 |
| N,N—Dimethylacetamide, DMSO, Neopentyl glycol | " | " | 1.49 | 1.59 |
| N,N—Dimethylacetamide, DMSO, 1,6-Hexanediol | " | " | 1.63 | 1.67 |
| N,N—Dimethylacetamide, DMSO, Hexylene glycol | " | " | 1.40 | 1.10 |
| N,N—Dimethylacetamide, DMSO, Diethylene glycol | " | " | 1.67 | 1.60 |
| N,N—Dimethylacetamide, DMSO, Triethylene glycol | " | " | 1.75 | 1.63 |
| N,N—Dimethylacetamide, DMSO, Tetraethylene glycol | " | " | 1.54 | 1.57 |
| N,N—Dimethylacetamide, DMSO, Dipropylene glycol | " | " | 1.48 | 1.87 |
| N,N—Dimethylacetamide, DMSO, Polyethylene glycol | " | " | 1.54 | 1.60 |
| N,N—Dimethylacetamide, DMSO, Glycerine | " | " | 1.35 | 1.20 |
| N,N—Dimethylacetamide, DMSO, 1,2,6-Hexanetriol | " | " | 1.39 | 1.30 |
| N,N—Dimethylacetamide, DMSO, Ethylene carbonate | " | " | 1.66 | 1.89 |
| N,N—Dimethylacetamide, DMSO, Propylene carbonate | " | " | 1.09 | 1.18 |
| N,N—Dimethylacetamide, DMSO, Triethanolamine | " | " | 2.08 | 1.41 |
| N,N—Dimethylacetamide, DMSO, Quinoline | " | " | 1.04 | 1.53 |
| N,N—Dimethylacetamide, 1,3-Propanediol | " | " | | |
| N,N—Dimethylacetamide, Dimethylformamide (DMFA), Ethylene glycol | " | " | 1.64 | 1.61 |
| N,N—Dimethylacetamide, DMFA, 1,5-Pentanediol | " | " | 1.32 | 1.15 |
| N,N—Dimethylacetamide, DMFA, 1,2,6-Hexanetriol | " | " | 1.26 | 1.52 |
| N,N—Dimethylacetamide, Ethylene glycol, Propylene glycol | " | " | 1.29 | 1.45 |
| N,N—Dimethylacetamide, Ethylene glycol, 1,4-Butanediol | " | " | 1.57 | 1.52 |
| N,N—Dimethylacetamide, Ethylene glycol, 1,5-Pentanediol | " | " | 1.32 | 1.24 |
| N,N—Dimethylacetamide, Ethylene glycol, Glycerine | " | " | 1.54 | 1.66 |
| N,N—Dimethylacetamide, Ethylene glycol, Ethylene carbonate | " | " | 1.43 | 1.53 |
| N,N—Dimethylacetamide, Glycerine, Propylene glycol | " | " | 1.20 | 1.56 |
| N,N—Dimethylacetamide, Glycerine, Ethylene carbonate | " | " | 1.48 | 1.64 |
| N,N—Dimethylacetamide, DMSO, Ethylene glycol, Glycerine | $(\frac{1}{4})^4$ | $(\frac{1}{4})^4$ | 1.42 | 1.76 |
| N,N—Dimethylacetamide, DMSO, 1,2,6-Hexanetriol, Nitrobenzene | " | " | 1.45 | 1.13 |
| N,N—Dimethylacetamide, Glycerine, Ethylene glycol, Adiponitrile | " | " | 1.19 | 1.22 |
| N,N—Dimethylacetamide, Glycerine, Ethylene glycol, Sulfolane | " | " | 1.22 | 1.21 |
| N,N—Dimethylacetamide, DMFA, Ethylene glycol, Glycerine | " | " | 1.45 | 1.47 |

TABLE 3

Extractive Distillation Agents That Are Efective in Separating
n-Butyl acetate From n-Butanol Which Contain Ethylene Glycol

| Compounds | Ratios | | Relative Volatilities | |
|---|---|---|---|---|
| Ethylene glycol | 1 | | 2.00 | |
| Ethylene glycol, Propylene glycol | (½)² | (3/5)² | 1.35 | 1.52 |
| Ethylene glycol, 1,4-Butanediol | " | " | 1.46 | 1.95 |
| Ethylene glycol, 1,6-Hexanediol | " | " | 1.29 | 1.31 |
| Ethylene glycol, Adiponitrile | " | " | 1.19 | 1.33 |
| Ethylene glycol, Dibutyl phthalate | " | " | 1.05 | 1.10 |
| Ethylene glycol, Ethylene carbonate | " | " | 1.51 | 1.47 |
| Ethylene glycol, Isophorone | " | " | 1.08 | 1.22 |
| Ethylene glycol, Sulfolane | " | " | 1.37 | 1.54 |
| Ethylene glycol, 1,4-Butanediol, Nitrobenzene | (⅓)³ | (2/5)³ | 1.03 | 1.08 |
| Ethylene glycol, Sulfolane, Propylene glycol | " | " | 1.16 | 1.35 |
| Ethylene glycol, Sulfolane, 1,4-Butanediol | " | " | 1.60 | 1.92 |
| Ethylene glycol, Sulfolane, 1,5-Pentanediol | " | " | 1.14 | 1.29 |
| Ethylene glycol, Sulfolane, Glycerine | " | " | 1.78 | 1.40 |
| Ethylene glycol, 1,4-Butanediol, Adiponitrile | " | " | 1.02 | 1.12 |
| Ethylene glycol, Glycerine, Ethylene carbonate | " | " | 1.63 | 1.56 |
| Ethylene glycol, Glycerine, Propylene carbonate | " | " | 1.22 | 1.13 |
| Ethylene glycol, Glycerine, Adiponitrile | " | " | 1.27 | 1.28 |
| Ethylene glycol, Glycerine, Adiponitrile, Glycerine | (¼)⁴ | (¼)⁴ | 1.02 | 1.10 |
| Triethanolamine, Propylene glycol | (½)² | (3/5)² | 1.46 | 1.26 |
| Triethanolamine, 1,4-Butanediol | " | " | 1.52 | 1.54 |
| Triethanolamine, 1,5-Pentanediol | " | " | 1.41 | 1.62 |
| Triethanolamine, 1,6-Hexanediol | " | " | 1.46 | 1.53 |
| Triethanolamine, 1,3-Propanediol | " | " | 1.31 | 1.48 |
| Triethanolamine, Diethylene glycol | " | " | 1.27 | 1.52 |
| Triethanolamine, Dipropylene glycol | " | " | 1.16 | 1.23 |
| Triethanolamine, Polyethylene glycol | " | " | 1.46 | 1.47 |
| Triethanolamine, Polypropylene glycol | " | " | 1.02 | 1.15 |
| Triethanolamine, Dimethylsulfoxide (DMSO) | " | " | 1.51 | 1.74 |
| Triethanolamine, DMSO, Ethylene glycol | (⅓)³ | (2/5)³ | 1.86 | 2.14 |
| Triethanolamine, DMSO, Propylene glycol | " | " | 1.61 | 1.72 |
| Triethanolamine, DMSO, 1,4-Butanediol | " | " | 1.56 | 1.74 |
| Triethanolamine, DMSO, 1,5-Pentanediol | " | " | 1.63 | 1.86 |
| Triethanolamine, DMSO, 1,6-Hexanediol | " | " | 1.70 | 1.74 |
| Triethanolamine, DMSO, 1,3-Propanediol | " | " | 1.59 | 1.62 |
| Triethanolamine, DMSO, Diethylene glycol | " | " | 1.59 | 1.67 |
| Triethanolamine, DMSO, Dipropylene glycol | " | " | 1.41 | 1.59 |
| Triethanolamine, DMSO, Polyethylene glycol | " | " | 1.46 | 1.46 |
| Triethanolamine, DMSO, Polypropylene glycol | " | " | 1.60 | 1.62 |
| Triethanolamine, DMSO, Dimethylformamide | " | " | 1.55 | 1.98 |
| Triethanolamine, Dimethylformamide, Ethylene glycol | " | " | 1.52 | 2.02 |

TABLE 4

Extractive Distillation Agents That Are Effective in Separating
n-Butyl acetate From n-Butanol Which Contain Triethanolamine

| Compounds | Ratios | | Relative Volatilities | |
|---|---|---|---|---|
| Triethanolamine, Propylene glycol | (½)² | (3/5)² | 1.46 | 1.26 |
| Triethanolamine, 1,4-Butanediol | " | " | 1.52 | 1.54 |
| Triethanolamine, 1,5-Pentanediol | " | " | 1.41 | 1.62 |
| Triethanolamine, 1,6-Hexanediol | " | " | 1.46 | 1.53 |
| Triethanolamine, 1,3-Propanediol | " | " | 1.31 | 1.48 |
| Triethanolamine, Diethylene glycol | " | " | 1.27 | 1.52 |
| Triethanolamine, Dipropylene glycol | " | " | 1.16 | 1.23 |
| Triethanolamine, Polyethylene glycol | " | " | 1.46 | 1.47 |
| Triethanolamine, Polypropylene glycol | " | " | 1.02 | 1.15 |
| Triethanolamine, Dimethylsulfoxide (DMSO) | " | " | 1.51 | 1.74 |
| Triethanolamine, DMSO, Ethylene glycol | (⅓)³ | (2/5)³ | 1.86 | 2.14 |
| Triethanolamine, DMSO, Propylene glycol | " | " | 1.61 | 1.72 |
| Triethanolamine, DMSO, 1,4-Butanediol | " | " | 1.56 | 1.74 |
| Triethanolamine, DMSO, 1,5-Pentanediol | " | " | 1.63 | 1.86 |
| Triethanolamine, DMSO, 1,6-Hexanediol | " | " | 1.70 | 1.74 |
| Triethanolamine, DMSO, 1,3-Propanediol | " | " | 1.59 | 1.62 |
| Triethanolamine, DMSO, Diethylene glycol | " | " | 1.59 | 1.67 |
| Triethanolamine, DMSO, Dipropylene glycol | " | " | 1.41 | 1.59 |
| Triethanolamine, DMSO, Polyethylene glycol | " | " | 1.46 | 1.46 |
| Triethanolamine, DMSO, Polypropylene glycol | " | " | 1.60 | 1.62 |
| Triethanolamine, DMSO, Dimethylformamide | " | " | 1.55 | 1.98 |
| Triethanolamine, Dimethylformamide, Ethylene glycol | " | " | 1.52 | 2.02 |

TABLE 5

Data From Runs Made In Rectification Column

| Agents | Wt. % n-Butyl acetate Overhead | Wt. % n-Butyl acetate Bottoms | Relative Volatility |
|---|---|---|---|
| Ethylene glycol | 96.78 | 57.65 | 1.99 |
| Dimethylsulfoxide (DMSO) + Acetamide 1:1 | 97.6 | 83.6 | 1.59 |
| DMSO (R) + Acetamide (R) + Dimethylformamide 1:1:1 | 93.31 | 78.11 | 1.35 |
| Ethylene glycol (R) + Propylene glycol (R) 1:1 | 95.79 | 75.65 | 1.56 |
| Ethylene glycol (R) + Propylene glycol (R) 1:1 + DMSO + Acetamide 1:1 | 94.69 | 76.53 | 1.46 |

Notes:
Feed mixture was 86% n-Butyl acetate, 11% n-Butanol, 3% Water.
Agents were added at 20 ml/min & 50° C.
(R) indicates that agents were reclaimed & reused. Compositions are calculated on agent-and water-free basis.
The number below the agent is its ratio in the mixture.

n-butyl acetate in the overhead and 57.65 wt.% in the bottoms, both on a water-free basis which gives a relative volatility of 1.99 of n-butyl acetate to n-butanol. This indicates that the ternary azeotrope has been negated and separation accomplished. The n-butyl acetate comes off in the form of its binary azeotrope with water which on condensation, immediately forms two liquid layers. The solubility of n-butyl acetate in liquid water is only 0.7%.

THE USEFULNESS OF THE INVENTION

The usefulness or utility of this invention can be demonstrated by referring to the data presented in Tables 1–5. All of the successful extractive distillation agents show that n-butyl acetate, n-butanol and water can be separated from their ternary azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity n-butyl acetate from any mixture of these three including the ternary minimum azeotrope. The stability of the compounds used and the boiling point difference is such that complete recovery and recycle is obtainable by a simple distillation and the amount required for make-up is small.

WORKING EXAMPLES

Example 1: The n-butyl acetate-n-butanol-water azeotrope is 63 wt.% n-butyl acetate, 8 wt.% n-butanol, 29 wt.% water. Fifty grams of the n-butyl acetate-n-butanol-water azeotrope and fifty grams of N,N-dimethylacetamide were charged to an Othmer type glass vapor-liquid equilibrium still and refluxed for nine hours Analysis of the vapor and liquid by gas chromatography gave vapor of 89.6% n-butyl acetate, 10.4% n-butanol; liquid of 80.9% n-butyl acetate, 19.1% n-butanol. This indicates a relative volatility of 2.03. Ten grams of N,N-dimethylacetamide were added and refluxing continued for another nine hours. Analysis indicated a vapor composition of 87.8% n-butyl acetate, 12.2% n-butanol, a liquid composition of 84% n-butyl acetate, 16% n-butanol which is a relative volatility of 1.38.

Example 2: Fifty grams of the n-butyl acetate-n-butanol-water azeotrope, 25 grams of acetamide and 25 grams of ethylene glycol were charged to the vapor-liquid equilibrium still and refluxed for eleven hours. Analysis indicated a vapor composition of 87.1% n-butyl acetate, 12.9% n-butanol, a liquid composition of 78% n-butyl acetate, 22% n-butanol which is a relative volatility of 1.90. Five grams of acetamide and five grams of ethylene glycol were added and refluxing continued for another thirteen hours. Analysis indicated a vapor composition of 80.8% n-butyl acetate, 19.2% n-butanol, a liquid composition of 70.1% n-butyl acetate, 29.9% n-butanol which is a relative volatility of 1.79.

Example 3: Fifty grams of the n-butyl acetate-n-butanol-water azeotrope, 17 grams of triethanolamine, 17 grams of DMSO and 17 grams of 1,4-butanediol were charged to the vapor-liquid equilibrium still and refluxed for 12 hours. Analysis indicated a vapor composition of 68.3% n-butyl acetate, 31.7% n-butanol, a liquid composition of 57.9% n-butyl acetate, 42.1% n-butanol which is a relative volatility of 1.56. Three grams each of triethanolamine, DMSO and 1,4-butanediol were added and refluxing continued for another 12 hours. Analysis indicated a vapor composition of 63.1% n-butyl acetate, 36.9% n-butanol, a liquid composition of 49.6% n-butyl acetate, 50.4% n-butanol which is a relative volatility of 1.74.

Example 4: A glass perforated plate rectification column was calibrated with ethylbenzene and p-xylene which possesses a relative volatility of 1.06 and found to have 4.5 theoretical plates. A solution of 430 grams of n-butyl acetate, 55 grams of n-butanol and 15 grams of water was placed in the stillpot and heated. When refluxing began, an extractive agent containing 50% ethylene glycol and 50% propylene glycol was pumped into the column at a rate of 20 ml/min. The temperature of the extractive agent as it entered the column was 50° C. After establishing the feed rate of the extractive agent, the heat input to the n-butyl acetate, n-butanol and water in the stillpot was adjusted to give a total reflux of 10–20 ml/min. After one hour of operation, the overhead and bottoms samples of approximately two ml. were collected and analysed using gas chromatography, The overhead analysis was 95.32% n-butyl acetate, 4.68% n-butanol. The bottoms analysis was 80.79% n-butyl acetate, 19.21% n-butanol. Using these compositions in the Fenske equation, with the number of theoretical plates in the column being 4.5, gave an average relative volatility of 1.42 for each theoretical plate. After 1½ hours of total operating time, the overhead and bottoms samples were taken again and analysed. The overhead composition was 95.79% n-butyl acetate, 4.21% n-butanol and the bottoms composition was 75.65% n-butyl acetate, 24.35% n-butanol. This gave an average relative volatility of 1.56 for each theoretical plate. After two hours of total operating time, the overhead and bottoms samples were again taken and analysed. The overhead composition was 95.31% n-butyl acetate, 4.69% n-butanol and the bottoms composition was 70.34% n-butyl acetate, 29.65% n-butanol. This gave an average relative volatility of 1.61 for each theoretical plate.

Example 5: A solution of 430 grams of n-butyl acetate, 55 grams of n-butanol and 15 grams of water was placed in the stillpot of the same column used in Example 4 and heat applied. When refluxing began, an extractive agent comprising 36% ethylene glycol, 36% propylene glycol, 18% DMSO and 10% acetamide was fed into the top of the column at a feed rate of 20 ml/min. and a temperature of 50° C. After establishing the feed rate of the extractive agent, the heat input to the n-butyl acetate, n-butanol and water in the stillpot was adjusted to give a total reflux rate of 10–20 ml/min. Having established the reflux rate, the column was allowed to operate for one hour. After one hour of steady operation, overhead and bottoms samples of approximately two ml. were collected and analysed using gas chromatography. The overhead analysis was 93.66% n-butyl acetate, 6.34% n-butanol, the bottoms analysis was 80.8% n-butyl acetate, 19.2% n-butanol. Using these compositions in the Fenske equation with the number of theoretical plates in the column being 4.5, gave an average relative volatility of 1.32 for each theoretical plate. After 1½ hours of total operation, the overhead composition was 94.69% n-butyl acetate, 5.31% n-butanol and the bottoms composition was 76.53% n-butyl acetate, 23.47% n-butanol. This gave an average relative volatility of 1.46 for each theoretical plate. After two hours of total operation, the overhead composition was 95.95% n-butyl acetate, 4.05% n-butanol and the bottoms composition was 72.63% n-butyl acetate, 27.37% n-butanol. This gave an average relative volatility of 1.63 for each theoretical plate.

The nature of the present invention having been described, what we wish to claim as new and useful and secure by Letters Patent is:

1. A method for recovering n-butyl acetate from a mixture of n-butyl acetate, n-butanol and water which comprises distilling a mixture of n-butyl acetate, n-butanol and water in a rectification column in the presence of an effective amount of an extractive agent, recovering essentially pure n-butyl acetate and water as overhead product and obtaining the extractive agent and n-butanol from the stillpot or reboiler, the extractive agent comprises at least acetamide.

2. The method of claim 1 in which the extractive agent comprises a mixture of acetamide and at least one of the group consisting essentially of: dimethylsulfoxide, dimethylformamide, ethylene glycol, propylene glycol, 1,3-propanediol, 1,4-butanediol, 1,5-pentanediol, 1,6-hexanediol, diethylene glycol, triethylene glycol, tetraethylene glycol, dipropylene glycol, polypropylene glycol, formamide, ethylene carbonate, propylene carbonate, triethanolamine, glycerine, and N,N-dimethylacetamide.

* * * * *